United States Patent [19]
Johnson et al.

[11] Patent Number: 4,897,348
[45] Date of Patent: Jan. 30, 1990

[54] RECOMBINANT MATERIALS AND METHODS FOR PRODUCING HUMAN CONNECTIVE TISSUE-ACTIVATING PEPTIDE-III AND ANALOGS THEREOF

[75] Inventors: Paul H. Johnson, Menlo Park; Nahid S. Waleh, Palo Alto, both of Calif.

[73] Assignee: SRI International, Menlo Park, Calif.

[21] Appl. No.: 117,916

[22] Filed: Nov. 4, 1987

Related U.S. Application Data

[63] Continuation of Ser. No. 646,259, Aug. 30, 1984, abandoned, which is a continuation-in-part of Ser. No. 526,369, Aug. 25, 1983, abandoned.

[51] Int. Cl.$^4$ .................... C12P 21/02; C12N 15/00; C12N 1/20; C12N 1/00
[52] U.S. Cl. .................... 435/69.1; 435/172.3; 435/320; 435/252.33; 435/69.2; 536/27; 935/13; 935/10; 935/29; 935/41
[58] Field of Search .................... 435/172.3, 320, 253, 435/70; 536/27; 935/9, 10, 29, 41, 13

[56] References Cited

U.S. PATENT DOCUMENTS 4,366,246  12/1982  Riggs .................... 435/172.3
4,568,640   2/1986  Rubin .................... 435/70

OTHER PUBLICATIONS

Castor et al, PNAS, U.S.A., vol. 80, pp. 765–769, Feb. 1983.
Caruthers et al, Genetic Engineering Principles and Methods, vol. 4, Ed. by Setlow et al, Plenum Press, pp. 1–17 (1982).
Selker et al, Journal of Bacteriology, vol. 129, pp. 388–394, Jan. 1977.
Yamada et al, PNAS, U.S.A., vol. 79, pp. 2827–2831, May 1982.
Gouz et al, Nucleic Acids Research, vol. 10, No. 22, pp. 7055–7074, Nov. 25, 1982.
Brot et al, Archives of Biochemistry and Biophysics, vol. 223, pp. 271–281, 1983.
Brot et al, TIBS, Apr. 1982.
Johnson et al, The Journal of Biological Chemistry, vol. 254, pp. 4022–4026, May 25, 1979.
Wilkinson et al, Nature, vol. 307, pp. 187–188, Jan. 1984.
Beatty et al, The Journal of Biological Chemistry, vol. 255, pp. 3931–3934, May 10, 1980.
Zoller et al, Nucleic Acids Research, vol. 10, pp. 6487–6500, 1982.

*Primary Examiner*—John E. Tarcza
*Attorney, Agent, or Firm*—Irell & Manella

[57] ABSTRACT

A synthetic structural gene encoding CTAP-III or CTAP-III-Leu21 including adaptors for the carboxy and amino terminal ends of the gene which contain start and stop codons and convenient restriction sites for use in cloning the gene is described. The gene was designed for efficient expression in bacteria and to include two unique restriction sites for BamHI and XbaI. Plasmid expression vectors that are derivatives of pBR322 that contain a ColE1 insert which includes the expression control sequence and structural gene for colicin are also described. Constructs for expressing CTAP-III, CTAP-III-Leu21, CTAP-III or CTAP-III-Leu21 having a nonpolar pentapeptide fused to its amino terminus, and fusion proteins of such CTAP-III proteins and a colicin fragment are prepared by inserting the synthetic structural gene into the vectors at positions in phase with the colicin expression control sequence and under the control thereof.

12 Claims, 12 Drawing Sheets

```
                        5                              10                             15                             20
Asn Leu Ala Lys Gly Lys Glu Glu Ser Leu Asp Ser Asp Leu Tyr Ala Glu Leu Ars Crs
AAG CTN GCN AAP GGN AAP GAP GAP TCN CTN GAG TCN GAG CTN TAG GCN GAP CTN CGN TGG
    TTP                         AGG TTP     AGG         TTP                 TTP AGP 25                             30                             35                             40
Met Crs Ile Lys Thr Thr Ser Gly Ile His Pro Lys Asn Ile Gln Ser Leu Glu Val Ile
ATG TGG ATG AAP ACN ACN TCN GGN ATG CAG CCN AAP AAG ATG CAP TCN CTN GAP GTN ATG
    ATA             AGG     ATA                     ATA     AGG TTP         ATA 45                             50                             55                             60
Gly Lys Gly Thr His Crs Asn Gln Val Glu Val Ile Ala Thr Leu Lys Asp Gly Ars Lys
GGN AAP GGN ACN CAG TGG AAG CAP GTN GAP GTN ATG GCN ACN CTN AAP GAG GGN CGN AAP
                                                ATA         TTP                 AGP 65                             70                             75                             80
Ile Crs Leu Asp Pro Asp Ala Pro Ars Ile Lys Lys Ile Val Gln Lys Lys Leu Ala Gly
ATG TGG CTN GAG CCN GAG GCN CCN CGN ATG AAP AAP ATG GTN CAP AAP AAP CTN GCN GGN
ATA     TTP                     AGP ATA         ATA                 TTP 85                             90                             95                            100
Asp Glu Ser Ala Asp
GAG GAP TCN GCN GAG
            AGG
```

```
                                              (Met Glu Thr Leu Met)
                                                                20
Asn Leu Ala Lys Gly Lys Glu Glu Ser Leu Asp Ser Asp Leu Tyr Ala Glu Leu Arg Cys
                            10                                  40
[Leu]
Met Cys Ile Lys Thr Thr Ser Gly Ile His Pro Lys Asn Ile Gln Ser Leu Glu Val Ile
                            30                                  60
Gly Lys Gly Thr His Cys Asn Gln Val Glu Val Ile Ala Thr Leu Lys Asp Leu Arg Ile
                            50                                  80
Ile Cys Leu Asp Pro Asp Ala Pro Arg Ile Lys Lys Ile Val Gln Lys Lys Leu Ala Gly
                            70                                 100
Asp Glu Ser Ala Asp
                            90
```

FIG. 1

```
      Asn Leu Ala Lys Gly Lys Glu Glu Ser Leu Asp Ser Asp Leu Tyr Ala Glu Leu Arg Cys
      AAG CTN GCN AAP GGN AAP GAP GAP TCN CTN GAG TCN GAG CTN TAG GCN GAP CTN CGN TGG
      TTP                             AGG TTP         AGG     TTP         TTP AGP
               5                      10                      15                      20

Met Cys Ile Lys Thr Thr Ser Gly Ile His Pro Lys Asn Ile Gln Ser Leu Glu Val Ile
      ATG TGG ATG AAP ACN ACN TCN GGN ATG CAG CCN AAP AAG ATG CAP TCN CTN GAP GTN ATG
              ATA                 AGG ATA                     ATA AGG         TTP ATA
              25                      30                      35                      40

Gly Lys Gly Thr His Cys Asn Gln Val Ile Ala Thr Leu Lys Asp Gly Arg Lys
      GGN AAP GGN ACN CAG TGG AAG CAP GTN ATG GCN ACN CTN AAP GAG GGN CGN AAP
              AGG                     ATA                 TTP         AGP
              45                      50                      55                      60

Ile Cys Leu Asp Pro Asp Ala Pro Arg Ile Lys Lys Ile Val Gln Lys Lys Leu Ala Gly
      ATG TGG CTN GAG CCN GAG GCN CCN CGN ATG AAP AAP ATG GTN CAP AAP AAP CTN GCN GGN
      ATA     TTP                     AGP ATA                         TTP
              65                      70                      75                      80

Asp Glu Ser Ala Asp
      GAG GAP TCN GCN GAG
              AGG
              85                      90                      95                      100

FIG. 2
```

```
                    10                       28                          43
AATTCAGCTG ATG AAC CTG GCT AAA GGT AAA GAA GAA TCT CTG GAC TCT GAC TTA
           Asn Leu Ala Lys Gly Lys Glu Glu Ser Leu Asp Ser Asp Leu 58                   73                       88                         103
TAC GCT GAA CTG CGT TGC CTG TGC ATC AAA ACT ACT TCT GGG ATC CAC CCG AAA
Tyr Ala Glu Leu Arg Cys Leu Cys Ile Lys Thr Thr Ser Gly Ile His Pro Lys 118                      133                         148                        163
AAC ATC CAG TCT CTG GAA GTT ATC GGT AAA GGC ACT TGC AAC CAG GTT GAA
Asn Ile Gln Ser Leu Glu Val Ile Gly Lys Gly Thr Cys Asn Gln Val Glu 178                      193                         208
GTT ATC GCT ACT CTG AAA GAC GGT CGT AAA ATC TGT CTA GAT CCG GAC GCT CCA
Val Ile Ala Thr Leu Lys Asp Gly Arg Lys Ile Cys Leu Asp Pro Asp Ala Pro 223                      238                         253                        268
CGT ATC AAG AAG ATC GTT CAG AAA CTG GCT GGT GAC GAA TCT GCT GAC TAA
Arg Ile Lys Lys Ile Val Gln Lys Leu Ala Gly Asp Glu Ser Ala Asp

284
TGA CTGCAGAATT
```

FIG. 3

Arrows mark 5' side of CLEAVAGE site unless site name is in brackets.
Brackets indicate only RECOGNITION site is known.

```
         10        20        30        40        50        60        70
AATTCAGCTGATGAACCTGGCTAAAGGTAAAGAAGAATCTCTGGACTTATACGCTGAACTGCGT
        ^         ^                   ^         ^
      AluI      EcoRII              EcoRI*    HinFI
      NspBI     ScrFI               HinFI     MboI
      PvuII 80        90       100       110       120       130       140
TGCCTGTGCATCAAAACTACTTCTGGGATCCACCCGAAAAACATCCAGTCTCTGGAAGTTATCGGTAAAG
                         ^
                       SfaNI   BamHI
                               [BinI]
                               DpnI
                               EcoRI*
                               FokI
                               MboI
                               XhoII 150       160       170       180       190       200       210
GCACTCACTGCAACCAGGTTGAAGTTATCGCTACTCTGAAAGACGGTAAAATCTGTCTAGATCCGGA
        ^                                                  ^    ^
      EcoRII                                             EcoRI* DpnI
      ScrFI                                                     EcoRI*
                                                                Xbal  HpaII
                                                                      MboI
                                                                      XhoII 220       230       240       250       260       270       280
CGCTCCACGTATCAAGAGATCGTTCAGAAAAAACTGGCTGGTGACGAATCTGCTGACTAATGACTGCAG
        ^         ^         ^                             ^               ^
      HsaI      DpnI      MboII                        [EcoP15]          PstI
                MboI                                    EcoRI*
                                                        HinFI  HphI
                                                        [HinFIII]
AATT
```

FIG. 4

```
           10         20         30         40         50
    AATTCAGCTG ATGAACCTGG CTAAAGGTAA AGAAGAATCT CTGGACTCTG
    TTAAGTCGAC TACTTGGACC GATTTCCATT TCTTCTTAGA GACCTGAGAC 60         70         80         90        100
    ACTTATACGC TGAACTGCGT TGCCTGTGCA TCAAAACTAC TTCTGGGATC
    TGAATATGCG ACTTGACGCA ACGGACACGT AGTTTTGATG AAGACCCTAG 110        120        130        140        150
    CACCCGAAAA ACATCCAGTC TCTGGAAGTT ATCGGTAAAG GCACTCACTG
    GTGGGCTTTT TGTAGGTCAG AGACCTTCAA TAGCCATTTC CGTGAGTGAC 160        170        180        190        200
    CAACCAGGTT GAAGTTATCG CTACTCTGAA AGACGGTCGT AAAATCTGTC
    GTTGGTCCAA CTTCAATAGC GATGAGACTT TCTGCCAGCA TTTTAGACAG 210        220        230        240        250
    TAGATCCGGA CGCTCCACGT ATCAAGAAGA TCGTTCAGAA AAAACTGGCT
    ATCTAGGCCT GCGAGGTGCA TAGTTCTTCT AGCAAGTCTT TTTTGACCGA 260        270        280
    GGTGACGAAT CTGCTGACTA ATGACTGCAG AATT
    CCACTGCTTA GACGACTGAT TACTGACGTC TTAA
```

FIG. 5

FRAGMENT 1

```
EcoR1      10          20          30          40          50
 1    *          3     *     5           *          7
AATTCAGCTGATGAACCTGGCTAAAGGTAAAGAAGAATCTCTGGACTCTG
    GTCGACTACTTGGACCGATTTCCATTTCTTCTTAGAGACCTGAGAC
         2     *          4     *          6     *

60          70          80          90         100
     *           9     *          11    *          13
ACTTATACGCTGAACTGCGTTGCCTGTGCATCAAAACTACTTCTGG
TGAATATGCGACTTGACGCAACGGACACGTAGTTTTGATGAAGACCCTAG
      8    *          10    *          12    *          14
                                                        BamH1
```

FRAGMENT 2

```
BamH1     110         120         130         140         150
 15   *          17    *     19          *          21   *
GATCCACCCGAAAAACATCCAGTCTCTGGAAGTTATCGGTAAAGGCACTCACTG
    GTGGGCTTTTTGTAGGTCAGAGACCTTCAATAGCCATTTCCGTGAGTGAC
         16    *          18    *          20    *     22

160         170         180         190         200
      23         *         25          *          27
CAACCAGGTTGAAGTTATCGCTACTCTGAAAGACGGTCGTAAAATCTGT
GTTGGTCCAACTTCAATAGCGATGAGACTTTCTGCCAGCATTTTAGACAGATC
     *          24    *          26    *          28
                                                       Xba1
```

FRAGMENT 3

```
Xba1      210         220         230         240         250
  29   *          31    *          33    *          35
CTAGATCCGGACGCTCCACGTATCAAGAAGATCGTTCAGAAAAAACTGGCT
     TAGGCCTGCGAGGTGCATAGTTCTTCTAGCAAGTCTTTTTTGACCGA
          30    *          32    *          34    *

260         270         280
      *           37
GGTGACGAATCTGCTGACTAATGACTGCAG
CCACTGCTTAGACGACTGATTACTGACGTCTTAA
     36    *          38
                     EcoR1
```

FIG. 6

FIG. 11 Construction of pNP6/CTAP-III-N MOD

FIG. 12 Construction of pNP6ΔRI/Col:CTAP-III-Leu21

RECOMBINANT MATERIALS AND METHODS FOR PRODUCING HUMAN CONNECTIVE TISSUE-ACTIVATING PEPTIDE-III AND ANALOGS THEREOF

CROSS-REFERENCE TO RELATED APPLICATION

This application is a continuation of application Ser. No. 646,259, filed Aug. 30, 1984, abandoned, which is a continuation-in-part of copending U.S. application Ser. No. 526,369, filed Aug. 25, 1983, abandoned.

DESCRIPTION

1. Technical Field

This invention is in the field of genetic engineering. More particularly, it relates to synthetic genes for human connective tissue-activating peptide-III and novel analogs thereof, plasmid vectors for cloning and expressing such genes, and the microbial production of connective tissue activating peptide-III and analogs thereof.

2. Background Art

Human connective tissue-activating peptides (CTAPs) are a group of naturally occurring polypeptides that are capable of activating connective tissue cells. These peptides are present in platelets and leukocytes and stimulate mitogenesis, glycosaminoglycan and hyaluronic acid synthesis, prostaglandin $E_2$ and cyclic AMP formation, plasminogen activator secretion, fibroblast chemotaxis, glucose transport and glycolysis. CTAPs are being investigated as pharmaceuticals for regenerating connective tissue (e.g., wound healing). Castor, C. W., et al, PNAS (USA) (1983) 80:765-769 reports the amino acid sequence of one CTAP, known as CTAP-III, and the biological characteristics of CTAP-III. The CTAP reported in these studies was obtained from platelets. While extraction from platelets is a useful way of obtaining small amounts of CTAP-III for research purposes, it would be an impractical way of generating large amounts of the peptide. In this regard, one object of the present invention is to provide the means for producing CTAP-III and CTAP-III analogs via bacterial expression. These means include novel synthetic genes encoding CTAP-III and CTAP-III analogs that are designed for efficient expression of CTAP-III in bacteria and expression plasmids that contain these genes in association with the colicin El expression control region.

A recombinant plasmid containing an exogenous gene under the control of the colicin El regulatory region is described by Selker, E., et al, *J. Bacteriol* (1977) 129:388-394.

U.S. Pat. No. 4,356,270 generally concerns the expression of genes that encode mammalian polypeptides and are composed of a majority of codons that are preferred for bacterial expression. Gouz, M. And Gautier, C., *Nucl Acids Res* (1983) 10:7055-7074 report codon usage data for gene expression in *E. coli*.

U.S. Pat. No. 4,366,247 generally describes recombinant materials and procedures for microbially producing fusion proteins of an exogenous polypeptide linked to an endogenous amino acid sequence via an amino acid that defines a specific cleavage site.

DISCLOSURE OF THE INVENTION

One aspect of the invention is a synthetic gene that encodes CTAP-III or an analog (mutein) of CTAP-III in which the methionine at position 21 is replaced with leucine (hereinafter called CTAP-III-Leu21) and comprises a DNA sequence whose coding strand has the following sequence:

```
AACCTGGCLAAPGGQAAPGAAGAATCQCTGGAQTCQGAQCTGTACGCLGA
ACTGCGLTGCJTGTGCATCAAPACQACQTCQGGHATCCAQCCGAAPAACA
TCCAGTCQCTMGAPGTLATCGGQAAPGGQACQCAQTGCAACCAGGTLGAA
GTLATCGCLACQCTGAAPGAQGGQCGQAAPATCTGCCTGGAQCCGGAQGC
LCCGCGQATCAAPAAPATCGTLCAGAAPAAPCTGGCLGGQGAQGAATCQG
CLGAQ,
``` wherein:

A = Adenine H = either T, C or G
G = Guanine J = either C or A
C = Cytosine L = either T or A
T = Thymine M = either C or G
P = either A or G
Q = either C or T.

A preferred embodiment of this gene comprises the DNA sequence

```
AACCTGGCTAAAGGTAAAGAAGAATCTCTGGACTCTGACTTATACGCTGA
TTGGACCGATTTCCATTTCTTCTTAGAGACCTGAGACTGAATATGCGACT
ACTGCGTTGCJTGTGCATCAAAACTACTTCTGGGATCCACCCGAAAAACA
TGACGCAACGKACACGTAGTTTTGATGAAGACCCTAGGTGGGCTTTTTGT
TCCAGTCTCTGGAAGTTATCGGTAAAGGCACTCACTGCAACCAGGTTGAA
AGGTCAGAGACCTTCAATAGCCATTTCCGTGAGTGACGTTGGTCCAACTT
GTTATCGCTACTCTGAAAGACGGTCGTAAAATCTGTCTAGATCCGGACGC
CAATAGCGATGAGACTTTCTGCCAGCATTTTAGACAGATCTAGGCCTGCG
TCCACGTATCAAGAAGATCGTTCAGAAAAAACTGGCTGGTGACGAATCTG
AGGTGCATAGTTCTTCTAGCAAGTCTTTTTTGACCGACCACTGCTTAGAC
CTGAC
GACTG,
``` where A, G, C, T and J are as defined previously and K is either G or T depending on J. When J is A and K is T, he gene encodes CTAP-III. When J is C and K is G, the gene encodes CTAP-II-Leu21.

Another aspect of the invention is a DNA fragment for use in microbially producing human CTAP-III or a mutein thereof in which the methionine at position 21 is replaced with leucine consisting of the above described structural gene preceded by the base pair

G
C and terminated by an adaptor fragment having the sequence

TAATGACTGCAG
ATTACTGACGTCTTAA.

Another aspect of the invention is a recombinant plasmid vector comprising a replicator, a phenotypic marker gene, the colicin El expression control sequence comprising a promoter, an operator site for repressor binding, a ribosome binding site, and translation start codon and the colicin El structural gene is correct reading phase with the expression control sequence.

A preferred embodiment of the above described recombinant plasmid vector is a pBR322 derivative comprising pBR322 and a DNA fragment that includes the colicin El expression control sequence and the structural gene for colicin El inserted into pBR322 at the PstI site of pBR322.

Another aspect of the invention is a linear recombinant plasmid that is useful for making an inducible plasmid expression vector that includes the above described CTAP-III gene prepared by:
(a) digesting the above described pBR322 derivative with SacII to obtain linear plasmid DNA;
(b) treating the linear plasmid DNA with bacteriophage T4 DNA polymerase in the presence of dTTP;
(c) treating the linear plasmid product of (b) with S1 nuclease:
(d) digesting the linear plasmid product of (c) with EcoRI; and
(e) recovering the large linear DNA plasmid fragment from the digest of (d).

Another aspect is a recombinant plasmid expression vector comprising a bacterial expression control sequence, the above described structural gene downstream of and in phase with the expression control sequence and under the control thereof, and a translation start codon preceding the structural gene and a translation stop codon terminating the structural gene.

Another aspect of the invention is E. coli transformed with the above described recombinant plasmid expression vectors.

Another aspect of the invention is a process for making CTAP-III or CTAP-III-Leu21 comprising growing the above described transformed E. coli in a culture medium and inducing expression of CTAP-III or CTAP-III-Leu21 thereby by adding an expression-inducing amount of an agent that induces the SOS system of E. coli to the culture medium.

Another aspect of the invention is a protein having CTAP-III activity comprising a mutein of CTAP-III wherein the methionine at position 21 of CTAP-III has been replaced by another amino acid.

Another aspect of the invention is a fusion protein comprising:
(a) a useful polypeptide joined by an amino acid residue that defines a specific cleavage site not present in the useful polypeptide to
(b) a colicin fragment that lacks the cytotoxicity of colicin but retains the charge properties of colicin.

Another aspect of the invention is a method of producing a useful heterologous polypeptide microbially comprising:
(a) growing bacterial transformants that produce the useful polypeptide in he form of the above described fusion protein;
(b) disrupting the transformants;
(c) contacting the disruptate with a solid phase cation exchange medium at a pH of about 9 to 10.5;
(d) separating unbound disruptate from the solid phase cation exchange medium;
(e) eluting the fusion protein from the cation exchange medium;
(f) cleaving the fusion protein at said cleavage site; and
(g) recovering the useful heterologous polypeptide from the cleaved product of step (f).

Another aspect of the invention is a protein having the biological activity of CTAP-III comprising a mutein of CTAP-III that is less susceptible to in vivo conversion to $\beta$-thromboglobulin ($\beta$-TG) than CTAP-III. In one embodiment of this aspect the mutein comprises CTAP-III having a nonpolar polypeptide fragment fused to its amino terminal end that preserves the alpha helical structure of said end. In another embodiment the mutein is CTAP-III having one or more of the amino acids defining the trypsin-sensitive site proximate the amino terminal end of CTAP-III deleted or replaced with another amino acid.

Another aspect of the invention is a cyanogen bromide insensitive mutein of a useful protein whose amino acid sequence contains at least one methionine that is not essential to the usefulness of the protein, said mutein having said methionine(s) replaced by another amino acid.

Still other aspects of the invention are compositions and methods for regenerating connective tissue that involve therapeutically effective amounts of the above described muteins that have CTAP-III activity.

BRIEF DESCRIPTION OF THE DRAWINGS

In the drawings:

FIG. 1 is the amino acid sequence of CTAP-III with the added pentapeptide of an N-terminal modified analog (called CTAP-III-NMOD) shown in braces and the Met→Leu replacement of CTAP-III-Leu21 shown in brackets;

FIG. 2 is the ambiguous nucleotide sequence coding for the CTAP-III amino acid sequence of FIG. 1. The nucleotide abbreviations used in FIG. 2 and elsewhere herein are those indicated above;

FIG. 3 is the nucleotide sequence of the coding strand of the preferred embodiment of the synthetic gene for CTAP-III-Leu21 including the 3'- and 5'-adaptor sequences for use in cloning and expressing the gene. The corresponding amino acid sequence is shown below the nucleotide sequence;

FIG. 4 is a restriction endonuclease cleavage map of the nucleotide sequence of FIG. 3;

FIG. 5 is the complete double-stranded sequence of the preferred synthetic gene for CTAP-III-Leu21 including the 3'- and 5'-adaptor sequences;

FIG. 6 is a diagram showing the ligation strategy for constructing the synthetic gene shown in FIG. 5;

MODES FOR CARRYING OUT THE INVENTION

Figure 7:
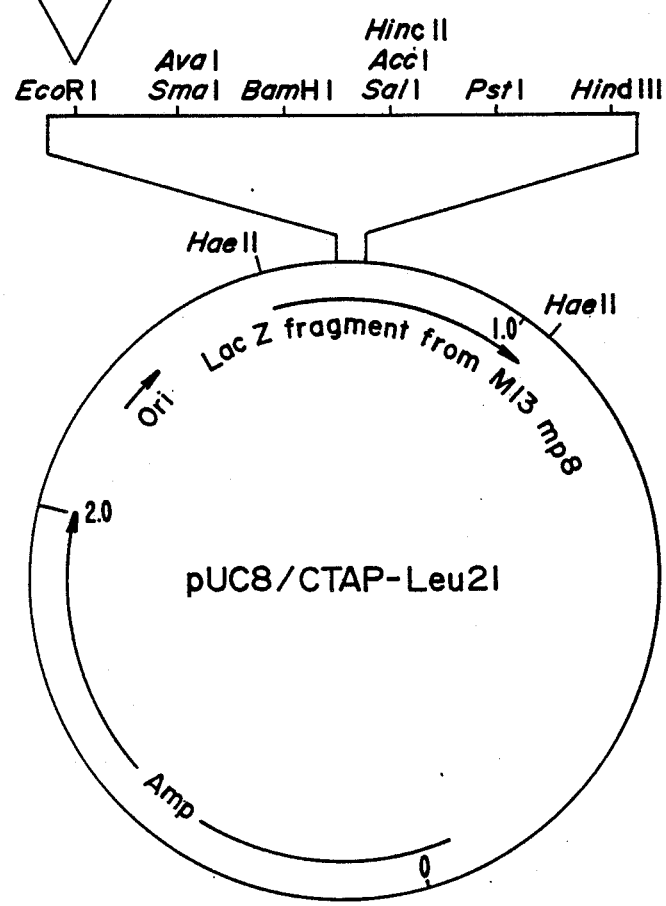
FIG. 7 is a diagram of the plasmid vector pUC8/-CTAP-III used in making an expression vector containing the synthetic gene of FIG. 5.

Several modifications of native human CTAP-III are included in the invention. One involves replacement of the methionine at position 21 of the CTAP-III amino acid sequence. The methionine may be replaced by an amino acid that does not affect the biological activity or stability of the molecule adversely. Amino acids having similar hydrophobic properties and acyclic side chains such as leucine, isoleucine, and valine are preferred. Leucine is a particularly preferred replacement. The replacement of the internal methionine renders the modified protein (modified molecules are commonly called analogs or muteins herein) insensitive to agents such as cyanogen bromide that cleave polypeptide chains specifically at methionine residues. Such insensitivity permits the mutein to be purified from cellular materials or extracts by digesting the materials or extracts with such agents or be separated from partner fusion sequences when the mutein is produced as a fusion protein in which it is linked to the partner by a methionine.

It will be appreciated that this aspect of the invention may be applied to useful polypeptides other than CTAP-III and CTAP-III analogs that contain one or more methionines that are not essential to the usefulness of the polypeptide. Deletion or replacement of the methionine(s) in such polypeptides may be achieved by synthesizing the gene encoding the methionine-depleted polypeptide from nucleotides or by site-specific mutagenesis of native or recombinant gene sequences.

Another modification of native CTAP-III involves altering the amino acid sequence in a manner that causes the resulting mutein to be less susceptible to in vivo conversion to β-TG than native CTAP-III without affecting biological properties adversely. Such alteration may involve the addition of a generally nonpolar polypeptide fragment to the amino terminus of native CTAP-III which fragment itself tends to form an alpha helical configuration and thus preserves the configuration of the terminus and/or deleting or replacing one or more of the amino acids that define the trypsin-sensitive site proximate to the amino terminus of native CTAP-III. Additions of nonpolar fragments to the amino terminus may be accomplished by synthesizing the gene to include codons for the fragment or by synthesizing the polypeptide in the form of a fusion protein in which the leader sequence or endogenous portion of the protein defines such a fragment. The fragment is composed predominantly of hydrophobic or ambivalent, acyclic amino acid residues such as leucine, methionine, and isoleucine. It may contain nonhydrophobic residues such as threonine and glutamine provided the fragment as a whole is nonpolar. The fragment need not be large and will, for convenience, normally contain 4 to 10 residues. Such modifications will prolong the in vivo half-life of the protein and, correlatively, its biological activity and therapeutic effectiveness. Deletion or replacement of one or more amino acids at the trypsin-sensitive site may be accomplished via de novo synthesis of the gene or by site-specific mutagenesis of native or recombinant CTAP-III genes.

Producing CTAP-III or CTAP-III muteins in the form of fusion proteins in which the endogenous portion of the protein is a biologically inactive colicin E1 fragment that possesses colicin's charge properties and the fusion site is readily cleavable is yet another modification. Such proteins may be produced using expression vectors in which the CTAP-III or CTAP-III mutein gene with suitable terminators is inserted into a vector containing the colicin expression control sequence and structural gene at a convenient restriction site near the end of the colicin structural gene that encodes the carboxy-terminus of colicin. The fusion protein retains the charge properties of colicin (colicin E1 has a high isoelectric point, >9.5, compared to most other bacterial proteins and thus binds to cation exchange media at high pHs whereas other bacterial proteins do not) whereby it may be easily isolated by ion exchange chromatography using a cation exchange medium at a pH of about 9 to 10.5, preferably about 9.5. Conventional cation ion exchange resins such as CM-cellulose, P-cellulose or SE cellulose or cross-linked dextran- or polyacrylamide-based ion exchange gels such as CM-Sephadex or SP-Sephadex may be used. The ionic strength used will depend upon the particular media used. Conventional ion exchange separation equipment (e.g., columns) and equilibrium and elution procedures are used in the separation.

After the fusion protein is separated by ion exchange chromatography the CTAP-III or CTAP-III mutein is separated by treating the fusion protein with a cleavage agent that cleaves the protein at the fusion site. For instance, when the two segments of the protein are fused via a methionine residue and a methionine-free mutein is involved, the protein may be treated with cyanogen bromide.

Those of skill in the art will also appreciate that fusion proteins of other useful polypeptides and colicin fragments may be made, separated by ion exchange chromatography and cleaved to provide the useful polypeptide in a similar manner.

Also, as is known in the art the CTAP-III and CTAP-III analogs that are produced via expression of recombinant DNA in bacteria may have an initial methionine residue at their amino terminus.

The CTAP-III and CTAP-III muteins (other than those rendered insensitive to trypsin) made by the invention may be converted to β-TG and β-TG muteins by treating them with trypsin or plasmin. β-TG is a chemotactic agent.

The following provides a detailed description of specific embodiments of the invention that involve CTAP-III, CTAP-III mutein and fusion proteins of a colicin fragment and a CTAP-III mutein.

DESIGN OF SYNTHETIC GENE FOR CTAP-III/CTAP-III-LEU21

The amino acid sequence of CTAP-III (FIG. 1) was reverse translated into the ambiguous coding sequence shown in FIG. 2 using the genetic code. The final unambiguous nucleotide sequence shown in FIG. 3 for the structural gene encoding CTAP-III-Leu21 was determined as follows.

The ambiguous nucleotide sequence was reduced to a single nonambiguous sequence by the selection of codons that are preferred for high levels of expression in bacteria. Changes were made to introduce two unique restriction sites into this sequence for the endonucleases BamHI and XbaI. These changes involve using nonoptimal codons for the Gly at position 28 (GGG), and the Leu at position 63 (CTA). These sites were added to permit alternative strategies for synthesizing the gene, sub-cloning the gene, confirming the sequence of the synthesized gene and modifying the gene to encode muteins (analogs). The resulting sequence was analyzed with a computer program designed to detect both complementary and repeated sequences. This information was used to identify regions of intrasequence homology that could interfere with the current ligation of oligonucleotides used to synthesize the gene and to modify the gene accordingly.

Adaptor sequences were designed for the termini of the structural gene to provide suitable start and stop signals, restriction sites, and cohesive EcoRI ends for cloning the gene as follows.

The adaptor sequence that was added to the carboxy-terminal coding end of the gene was designed to include two tandem translation termination condons (TAA, TGA), a PstI recognition sequence (CTGCAG), and part of an EcoRI recognition sequence (AATT). The adapter sequence that was added to the amino-terminal end of the gene was designed to include a translation start codon (ATG), a PuvII recognition sequence (CAGCTG), and part of an EcoRi recognition sequence (AATT).

The final sequence was analyzed by computer to verify that the sequence could be translated to give the correct amino acid sequence for the CTAP-III-Leu21 protein. A restriction endonuclease map of the structural gene plus adapter sequences for all known enzymes is shown in FIG. 4. The arrows mark the 5'-side of the cleavage site unless the site name is in brackets. Brackets indicate that only the recognition site is known.

GENE SYNTHESIS

Strategy and Oligonucleotide Preparation

FIG. 5 shows the complete DNA sequence for the synthetic CTAP-III-Leu21 structural gene plus adapter sequences. As shown in FIG. 6, the gene was divided into three fragments: fragment I EcoRI to BamHI,k fragment II BamHI to XbaI and fragment III XbaI to EcoRI. Each fragment was further divided into small oligonucleotides as indicated. There were 38 oligonucleotides in all. The asterisks in FIG. 6 indicate the oligonucleotide boundaries. The oligonucleotides were synthesized by the phosphotriester method (Ohtsuka, E., et al, *Nucleic Acid Res* (1982) 10:6553–6570). The crude oligonucleotides were purified by ion-exchange HPLC with a 30–45 min gradient of 0.1M–0.4M $KH_2PO_4$ buffer containing 20% acetonitrile. The product peaks were collected, desalted, dried and reconstituted in distilled $H_2O$. The size and homogeneity of the purified oligonucleotides were confirmed by gel electrophoresis using 20% acrylamide gels with 3–3.5% cross linker. Oligonucleotides with less than 95% purity were further purified to the desired purity level either by reverse-phase HPLC or by preparative gel electrophoresis.

LIGATIONS

Fragment I

Oligonucleotides 1–14 (FIG. 6) were individually radiolabeled in a reaction with $^{32}P$-ATP and polynucleotide kinase using the following protocol:

| | |
|---|---|
| Oligonucleotides | 0.04 OD |
| $^{32}P$-ATP (10 μCi/mmole) | 10 μl |
| Kinase/ligase buffer | 15 μl |
| (50 mM Tris-HCl (pH 7.6), 10 mM $MgCl_2$, dithiothreitol) | 10 mM |
| Polynucleotide Kinase | 1 μl |

The oligonucleotides and ATP were dried and dissolved in kinase buffer. The enzyme was added and incubated at 37° C. for 1 hr. The kinased oligonucleotides were combined into a single vial and placed in a 95° C. water bath for 10 min and then the bath was allowed to cool slowly to room temperature. 10×solution of 100 mM DTT/10 mM ATP was added followed by 5 units of T4 DNA ligase. The reaction mixture was incubated at 12° C. overnight (~16 hr).

The entire reaction mixture was purified on a 15% 1.5 mm nondenaturing polyacrylamide gel overnight, run at 250 volts. The product was located by autoradiography in comparison with a HaeIII digest of pBR322 DNA. The appropriate region on the gel was transferred to DE 81 paper by electrophoresis (Transblot). The appropriate band was then eluted from the paper using 1M NaCl in TE buffer. The DNA was ethanol precipitated and dissolved in water.

An aliquot of the product was checked for homogeneity on an analytical denaturing 15% polyacrylamide gel. Another aliquot was treated with DNA ligase to promote self-ligation of the product (5–6 hr at 4° C.). Then the reaction mixture was treated with EcoRI and BamHI and the reaction mixtures were analyzed by analytical gel electrophoresis. The product band was then cloned and sequenced.

Fragment II

Oligonucleotides 15–28 were kinased and ligated using the above procedure. The yield in this reaction was low. So this group was divided into two sub-groups (IIA, 15–21, and IIB, 22–28) and were ligated separately. Products from these two sub-groups were then ligated. The final product (103 bp) was subjected to self-ligation and treatment with appropriate restriction enzymes. The material was then cloned and sequenced.

Fragment III

Oligonucleotides 29–39 were kinased and ligated. The product, when analysed on analytical gel showed 3 bands (close to each other). Self-ligation and treatment with XbaI and EcoRI showed that only one of the 3 bands behaved as expected. This band was cloned and sequenced.

M13 CLONING/SEQUENCING

Synthetic fragment I (EcoRI, BamHI) was cloned into M13 mp8 and sequenced. Three of 16 independent clones had the correct sequence. The others had at least one base substitution.

Synthetic fragment II (BamHI, XbaI) was cloned into M13 mp11 and sequenced. The correct sequence was verified on 14 of 16 independent clones. The other two had a single base substitution.

Synthetic fragment III (XbaI, EcoRI) was cloned into M13 mp11 and sequenced. Eight of eight clones had the correct sequence.

ASSEMBLY OF COMPLETE GENE

Single stranded M13 for cloned fragments I or II were made double stranded with the universal primer and Klenow polymerase, then digested with EcoRI and BamHI for fragment I or BamHI and XbaI for fragment II. The inserts were electroeluted from a 6% acrylamide mini slab gel and ligated with EcoRI XbaI cut mp8. Several transformants were identified that had the correct (I+II) insert.

Single stranded M13 for cloned fragment (I+II) and III were double stranded as before and digested with EcoRI and XbaI. The purified inserts were gel purified, electroeluted and combined and ligated into EcoRI cut mp8. Seven clones were identified with the correct (I+II+III) insert. Both orientations were present.

Single stranded M13 with the I+II+III insert was double stranded as described and digested with EcoRI. A 284 bp insert was purified from the digest by gel electrophoresis.

CLONING OF THE SYNTHETIC CTAP-III-LEU21 GENE FRAGMENT IN PUC8

Approximately 5 µg of plasmid pUC8 (P-L Biochemicals, Milwaukee, WI) was digested for 60 min at 37° C. with EcoRI in a 50 µl solution containing 50 mM Tris-HCl (pH 7.5), 6 mM MgCl$_2$, 50 mM NaCl, and 1 mM DTT. Reactions were terminated by adding EDTA to a final concentration of 20 mM, then extracted with phenol/chloroform (3/1) and precipitated with ethanol.

Ten pmol of the synthetic gene fragment and 1 pmol (2.5 µg) of EcoRI-digested pUC8 plasmid DNA were ligated in a volume of 100 µl of 20 mM Tris-HCl (pH 7.6), 10 mM MgCl$_2$, 10 mM DTT, 5 mM ATP, and 10 units of T4 DNA ligase at 10° C. for 16 hr. Aliquots (5 µl) of the reaction mixture were used directly for transformation as described below.

The host for transformation experiments was *E. coli* K-12 strain JM83, which carries the lac Z$\Delta$M15 on a$\phi$80 integrated into the chromosome (ara, $\Delta$lac-pro, str A, thi, $\phi$80 lac Z$\Delta$M15) (U. Messing, "A multi-purpose cloning system based on the single-stranded DNA bacteriophage M13", *Recombinant DNA Technical Bulletin, NIH Publication No. 79-99*, 2, (1979) No. 2:43-48).

An overnight culture grown in L-broth (per liter: 10 g tryptone, 5 g yeast extract, 10 g NaCl, 2 ml 1.0 NaOH, and 10 ml 20% glucose added after autoclaving) was diluted 1:100 into fresh L-broth medium and was incubated with shaking at 37° C. until the OD$_{600}$ was 0.6. At that time, 35 ml of culture was centrifuged at 6,000 rpm for 10 min at 4° C. and the pellet resuspended in 10 ml of 0.05M CaCl$_2$. The cells were incubated on ice for 15 min before they were collected by centrifugation at 4,000 rpm for 10 min. The cells were then resuspended in 4 ml of 0.05M CaCl$_2$ and mixed with 200 µl of a DNA solution prepared by adding 5 µl of the ligation mixture (see above) and 150 µl 10 mM Tris-HCl (pH 7.5) containing 10 mM MgCl$_2$ and 10 mM CaCl$_2$. This mixture was incubated at 0° C. for 25 min. followed by incubation at 50° C. for 10 sec and at room temperature for 10 min. At that point, 14 ml of L-broth was added, and the culture mixture was shaken at 37° C. for 30 min. Then, 480 µl of ampicillin solution 1.25 mg/ml, was added to the culture, and the incubation was continued for another 30 min. Aliquots of 100 µl were plated on freshly prepared agar plates containing 2YT (per liter: 16 g Bacto tryptone, 10 g Bacto yeast extract, and 5 g NaCl) with 50 µl of 50 mg/ml ampicillin and 50 µl of 2% Xgal (5-bromo-4-chloro-3-indolyl-$\beta$-D-galactoside) added to each plate just before use.

Plates were incubated at 37° C. until colonies were between 0.5 and 2 mm in diameter. Bacteria containing plasmids without inserts make blue colonies on these indicator plates (containing Xgal), whereas those containing recombinant plasmids make white colonies. Several white colonies were screened directly for the presence of recombinant plasmid by analyzing a small amount of cleared lysate by agarose gel electrophoresis. Single colonies were grown in 1 ml of L-broth medium overnight at 37° C. Each culture was centrifuged for 5 min in an Eppendorf microcentrifuge, and the pellet was resuspended in 325 µl 10 mM Tris-HCl buffer, pH 7.5, containing 1.0 mM EDTA and 10 mM NaCl (TEN buffer). Eighty µl of 0.25M EDTA and 40 µl of 10% sodium dodecyl sufate (SDS) were added, and the mixture was incubated at 65° C. for an additional 5 min, followed by incubation on ice for 3 hr. After this period, the mixture was centrifuged in an Eppendorf microcentrifuge for 15 min. The supernatant was extracted with phenol, and the nucleic acid was precipitated with ethanol. The precipitate was redissolved in 50 µl TEN buffer. Five µl of this solution was digested with EcoRI, as described previously, and analyzed using 5% polyacrylamide slab gel electrophoresis. The size of the insert, as determined by measuring its electrophoretic migration versus a set of DNA fragments of known size, was approximately 285 base-pairs. The recombinant plasmid containing this insert was called pUC8/CTAP-III-Leu21. FIG. 7 is a diagram of the plasmid showing the location of the CTAP-III-Leu21 insert. A sample of the transformed *E. coli* containing this plasmid was deposited in the American Type Culture Collection (ATCC) 12301 Parklawn Drive, Rockville, Maryland, USA 20852 on 09 August 1984. This sample was assigned ATCC accession no. 39793. The deposit was made under the Budapest Treaty and will be maintained and made accessible to others in accordance with the provisions thereof.

The complete nucleotide sequence of the insert was confirmed using Sanger's enzymatic sequencing technique. (Sanger, F., *PNAS* (USA) (1977) 74:5463-5467.)

PREPARATION OF PLASMID VECTORS PNP6, PNP6$\Delta$RI, AND PNP6-LBR

The general scheme that was used to construct pNP6 and its derivatives, pNP6 RI and pNP6-LBR, was as follows. Open circular ColEl-K30 DNA molecules were sheared to give a normal distribution of DNA fragments with an average size of 2,000 base-pairs. These fragments were cloned into the single PstI site of the ampicillin locus of pBR322, using terminal transferase and the poly(G):poly(C) tailing procedure (Bolivar, F., et al, *Gene* (1977) 2:95-113). The resulting recombinant plasmids were then used to transform an *E. coli* K-12 strain wild-type for the inducible DNA repair (SOS) systems. Tetracycline-resistant (Tc$^r$) ampicillin-sensitive (Ap$^s$) transformant colonies that produced colicin (Col+) were selected and their plasmid DNAs analyzed. pNP6 and its derivatives have several advantages over the ColEl parent plasmid when used as expression vectors to produce exogenous polypeptides. The parent plasmid contains the colicin El immunity gene and a lysis gene. Induction of cells containing vectors based on the parent plasmid can result in cell lysis due to the activation of the lysis gene. In pNP6 the lysis gene and immunity gene are absent. Thus, induction will not cause cell lysis. Also, cells transformed with recombinant vectors in which a structural gene, such as the CTAP-III gene, has been inserted into the ColEl gene will not produce colicin El. This permits such transformants to be discerned from cells transformed with vectors that do not contain an insert, since the latter product colicin which kills the cells.

Plasmid pNP6 (FIG. 8) a Tc$^r$ Ap$^s$ Col+ recombinant plasmid, which has a molecular weight of $5.0 \times 10^6$ daltons and carries an insert of approximately 3,300 bp, was chosen for use as an expression vector. The plasmid carries the regulatory region (promoter, operator, and ribosome binding site) and the structural gene for colicin El. The nucleotide sequence for this region and gene are described by Yamada, M., et al, PNAS (USA) (1982) 79:2827–2831. Plasmid pNP6 can be cleaved into a linear molecule with SacII. The only SacII site of plasmid pNP6 is located 8 bp from the start of the colicin El gene. Exogenous (foreign) genes cloned into this site are under control of the colicin El regulatory sequence. Gene expression can be selectively induced by treating transformants with mitomycin C or other SOS system activating agents such as alkylating agents and the like.

Plasmid pNP6ΔRI is a derivative of pNP6 in which the EcoRI site in the pBR322 portion of the plasmid has been eliminated, thus leaving the plasmid with a unique EcoRI site located 19 codons upstream from the carboxy-terminus of the colicin structural gene. This plasmid is useful for making expression vectors for producing fusion proteins of the colicin fragment (lacing the 19 carboxy-terminus amino acids) and CTAP-III or analogs of CTAP-III. pNP6ΔRI was constructed by: partially digesting pNP6 with EcoRI: filling in the single stranded EcoRI ends of the linearized plasmid using a DNA polymerase reaction; blunt end ligating the resulting fragment; and identifying constructs that contain the colicin gene using the procedure described above.

The construction of plasmid pNP6-LBR, which may be used to make an expression vector containing the synthetic CTAP-III gene or CTAP-III analog genes, involves the following steps. pNP6 was first cleaved into a linear molecule (pNP6-L) by SacII endonuclease. pNP6-L is then treated with T$_4$ polymerase in the presence of dTTP followed by treatment with S1 nuclease to form a blunt ended linear molecule (pNP6-LB). pNP6-LB was next cleaved with EcoRI endonuclease to remove the segment of DNA from the remainder of the fifth codon of the colicin El gene to the EcoRI site in the pBR322 portion of pNP6 (pNP6-LBR).

Details of the construction of these plasmids follow.

ISOLATION OF COLEL PLASMID

Strain JC411 (Col EL-D30) was grown in 60 liters of M9 medium (per liter: 1 g NH$_4$Cl, 6 g Na$_2$HPO$_4$·H$_2$O, 3 g KH$_2$PO$_4$, 5 g NaCl, 3 g casamino acids, 1 ml 10% MgSO$_4$ supplemented with 10 ml 20% glucose and 0.5 ml 1M CaCl$_2$ added after autoclaving) in a fermentor at 37° C. to a cell density of approximately $5 \times 10^8$ CFU/ml. Chloramphenicol was added to a final concentration of 100 µg/ml, and the incubation at 37° C. was continued for another 6 hr. Cells were recovered using a Sharpels continuous-flow centrifuge. Then g (wet weight) of the pellet was suspended in 180 ml of 50 mM Tris-HCl buffer (pH 8.0) containing 50 mM EDTA and 15% sucrose. Then, 0.14 g of lysozyme was added, and the mixture was allowed to stand at room temperature for 10 min. Next, 16 ml of 10% SDS and 20 ml of 5M potassium acetate were added. The mixture was incubated on ice for 30 min and then centrifuged at 12,000 rpm for 30 min using the SS-34 rotor and a Sorvall centrifuge. Four mg of pancreatic ribonuclease A was added to the supernatant and the mixture was incubated at 37° C. for 1 hr. The sample was extracted twice with an equal volume of phenol saturated with 0.1M Tris, pH 8.0, and the DNA was precipitated by adding 1/10 sample volume of 3.0M sodium acetate and 2.5 volumes of cold ethanol, followed by an overnight incubation at −20° C. The resulting precipitate was recovered by centrifugation at 7,000 rpm for 50 min in a refrigerated Sorvall centrifuge using an HB-4 rotor. The pellet was dissolved in 50 ml of 10 mM Tris-HCl buffer (pH 7.5) containing 0.3M NaCl and 5 mM EDTA (NE Buffer). This sample was then applied to a Bio-Gel A.5 column (Bio-Rad Laboratories, Richmond, California), $5 \times 100$ cm, equilibrated with NE buffer. The DNA was eluted with NE buffer. Twenty-ml fractions were collected at a flow rate of 60 ml/hr. The elution of DNA was monitored by measuring the absorbance of each fraction at 260 nm using a Gilford 2600 UV-VIS spectrophotometer. The host DNA and the plasmid DNA was recovered together in the void volume. The fractions containing the DNA were pooled and precipitated with ethanol. The precipitate was collected by centrifugation at 8,000 rpm for 40 min in a refrigerated Sorvall centrifuge using an HB-4 rotor and redissolved in 5 ml 10 mM Tris-HCl buffer (pH 7.8) containing 0.2M NaCl. The DNA sample was then applied to an RPC-5 column, $0.9 \times 90$ cm, and packed under pressure at 30° C. The DNA was eluted with a linear gradient (total volume, 1 liter) of 0.6–0.7M NaCl in 10 mM Tris-HCl buffer, pH 7.8. Fractions of 2.5 ml were collected at a flow rate of 0.8 ml/min. The elution of DNA was monitored by measuring the conductivity of each collected sample using a conductivity meter (Radiometer, Copenhagen), and by agarose gel electrophoresis using vertical agarose slab gels ($0.25 \times 14 \times 15.5$ cm). The samples were applied to 1% agarose gels prepared in 40 mM Tris base buffer, pH 8.2, containing 1 mM EDTA and 5 mM sodium acetate (TAE buffer), and electrophoresed for 3 hr at a constant applied voltage of 5 V/cm. Fractions containing the supercoiled and the nicked circular DNA were pooled separately and were precipitated with cold ethanol. The resulting precipitates of ColEl DNA molecules were dissolved in 1.0 and 0.6 ml TEN buffer, respectively.

ISOLATION OF PLASMID PBR322

Plasmid pBR322 was isolated from *E. coli* strain 294 (pBR322) by the procedure used for isolating ColEl plasmid described above. PREPARATION OF SHEARED FRAGMENTS OF COLEL DNA Two hundred μl of nicked circular ColEl DNA (0.7 μg/μl) and 2.8 ml of 0.3M sodium acetate were mixed. The DNA solution was placed in the microhomogenizer cell of an Omnimixer (Dupont Instruments, Newton, Connecticut), and the DNA was sheared at 38,500 rpm for 20 min. The temperature was kept at 0° C. throughout the shearing process. The sheared DNA was precipitated with ethanol, redissolved in 100 μl of TEN buffer, and treated with calf intestinal phosphatase (CIT) (Boehringer Mannheim, Indianapolis, Indiana). The treatment with CIT was carried out in two 500 μl reaction mixtures. Each reaction mixture contained 380 μl distilled water, 50 μl 1M Tris-HCl buffer (pH 8.0), 5 μl 10 mM zinc sulfate, 5 μl CIT (10 U/μl). After incubation at 37° C. for 30 min, an additional 5 μl of CIT was added and the incubation at 37° C. continued for another 30 min. The reaction mixtures were extracted twice with an equal volume of buffer-saturated phenol, and the DNA was precipitated with ethanol. The heterogeneous population of DNA fragments was further purified and separated according to size by sucrose gradient velocity centrifugation. A discontinuous sucrose gradient was prepared by sequential layering of 3.4 ml of 20%, 15%, 10%, and 5% sucrose in 0.3M sodium acetate buffer (pH 7.0) containing 1 mM EDTA in centrifuge tubes for the SW40 rotor (Beckman). The DNA sample in 100 μl (0.25 μg/μl) was layered on the sucrose gradient and centrifuged at 35,000 rpm for 20 hr at 10° C. using an L8-70 Beckman ultracentrifuge. Fractions of 0.5 ml each were collected and preipitated with ethanol. The precipitates were redissolved in 50 μl of TEN buffer and analyzed by agarose gel electrophoresis. DNA fragments generated by the treatment of bacteriophage DNA with HindIII endonuclease were used as molecular-weight standards. The λ/HindIII reaction mixture contained 27 μl distilled water, 10 μl 5X HindIII buffer (100 mM Tris-HCl, pH 7.4, 2.5 mM $Na_2$ EDTA, 200 mM NaCl, 5 mM DTT), 1 μl λDNA (0.7 μg/μl), and 2 μl HindIII solution (2 U/μl).

Sucrose gradient fractions containing sheared ColEl DNA fragments averaging 2,000 bp, were pooled, precipitated with ethanol, and redissolved in TEN buffer.

CLONING OF SHEARED COLEL FRAGMENTS IN PBR322

Plasmid pBR322 was cleaved into a linear molecule with PstI. The reaction mixture contained 520 μl distilled water, 200 μl 5X PstI buffer (50 mM Tris-HCl, pH 7.4, 0.5 mM $Na_2$ EDTA, 50 mM NaCl, 5 mM DTT, 50% glycerol, 0.15% Triton X100), 200 μl pBR322 DNA solution (0.25 μg/μl), and 80 μl PstI (12 U/μl), and was incubated at 37° C. for 4 hr. The reaction was stopped by adding EDTA to 20 mM and extracted with an equal volume of phenol. The DNA was precipitated with ethanol and redissolved in TEN buffer.

Poly(dG) homopolymer extensions were added to linear pBR322 molecules in a reaction mixture containing 6 μl distilled water, 20 μl 500 mM potassium cacodylate, 10 μl 10 mM cobalt chloride, 10 μl 1 mM DTT, 2 μl 10 mM dGTP, 20 μl $^3$H-dGTP (New England Nuclear Corporation), 25 μl DNA (0.04 μg/μl), and 5 μl (12 U/μl) terminal deoxynucleotidyl transferase (Bethesda Research Laboratories, Inc., Gaithersburg, Maryland).

Poly(dC) homopolymer extensions were added to ColEl sheared fragments in a similar reaction mixture, except that the total DNA was 2.0 μg and the nucleotide triphosphate was dCTP. The above reactions were carried out at 37° C. for 2 and 3 min, respectively, and were stopped by adding EDTA to 20 mM and extracting with phenol. ColEl-[poly(dC)]fragments were redissolved in 115 μl distilled water and were annealed to linear pBR322-[poly(dG)] molecules by adding 40 μl 0.5M NaCl, 40 μl 50 mM EDTA (pH 7.25), and 3 μl linear pBR322-[poly(dG)] DNA solution (0.1 μg/μl). The annealing mixture was incubated at 70° C. for 15 min and then cooled to 40° C. over a 5-hr period. The mixture was kept at 45° C. overnight, then cooled to room temperature.

For transformation into *E. coli* 294, an overnight culture grown in L-broth was diluted 1:100 into fresh L-broth medium and incubated with shaking at 37° C. until the $OD_{600}$ was 0.6. At this time, 35 ml of culture was centrifuged at 6,000 rpm for 10 min at 4° C., and the pellet was resuspended in 20 ml of 0.05M $CaCl_2$. The cells were incubated on ice for 15 min before they were collected by centrifugation at 4,000 rpm for 10 min. The cells were resuspended in 4 ml of 0.05M $CaCl_2$ and mixed with 200 μl of a DNA solution prepared by adding 50 μl of the annealing mixture and 150 μl 10 mM Tris-HCl (pH 7.5). containing 10 mM $MgCl_2$ and 10 mM $CaCl_2$. This mixture was incubated at 0° C. for 25 min, followed by incubation at 50° C. for 10 sec and at room temperature for 10 min. At this point, 14 mL of L-broth was added and the culture was shaken at 37° C. for 30 min. Then, 480 μl of tetracycline solution, 1.25 mg/ml, was added to the culture, and the incubation was continued for another 30 min. Aliquots of 100 μl were plated on freshly prepared agar plates containing 25 mL L-broth 1.5% agar and 25 μg/ml tetracycline. The $Tc^r$ transformants were further tested for sensitivity to ampicillin by plating on agar containing 25 μg/ml ampicillin.

The $Tc^r$ $Ap^s$ transformant colonies were then screened for the spontaneous production of colicin. Single colonies were spotted on L-agar plates and were incubated at 37° C. overnight. The colonies were killed by exposing them to chloroform vapor, then overlayed with 5 ml L-broth containing 0.7% agar and 0.1 ml of an overnight culture of *E. coli* K-12, CL142. After the agar was allowed to harden, the plates were incubated at 37° C. overnight. Colonies with a zone of inhibition around them were scored as colicin producers.

The $Tc^r$ $Ap^s$ $Col^+$ transformant colonies were screened for the presence of recombinant plasmids by analyzing a small amount of cleared lysate by agarose gel electrophoresis as described above with respect to pUC8/CTAP-III. The size of the plasmids were determined by measuring the electrophoretic migration of DNA through an agarose gel using 8 plasmid standards, ranging in size from $1.36 \times 10^6$ to $35.8 \times 10^6$ daltons (F. L. Marcina, D. J. Kopecko, K. R. Jones, D. J. Ayers, and S. M. McCowen. "A multiple plasmid-containing *Escherichia coli* strain: Convenient source of size reference plasmid molecules" *Plasmid* (1978) 1:417-420).

RESTRICTION ENDONUCLEASE FRAGMENT-SIZE ANALYSIS OF RECOMBINANT PLASMIDS

Transformed clones were grown in 2-liter cultures. Cleared lysates were prepared as described above. The supernatants were treated with pancreatic RNase A (100 μg/ml at 37° C. for 30 min) and then were extracted with phenol. The DNA was precipitated with ethanol and redissolved in TEN buffer.

Restriction enzymes were obtained as commercial preparations from Bethesda Research Laboratories, Inc. (BRL). The DNA was digested with PstI, EcoRI, SmaI, and SacII, using the conditions specified by BRL. Samples were applied to 1% agarose gels and electrophoresed for 4 hr at a constant applied voltage of 5 V/cm. The molecular weights of restriction fragments were determined relative to the standard migration patterns of bacteriophase λDNA digested with HindIII and HaeIII.

Figure 8:
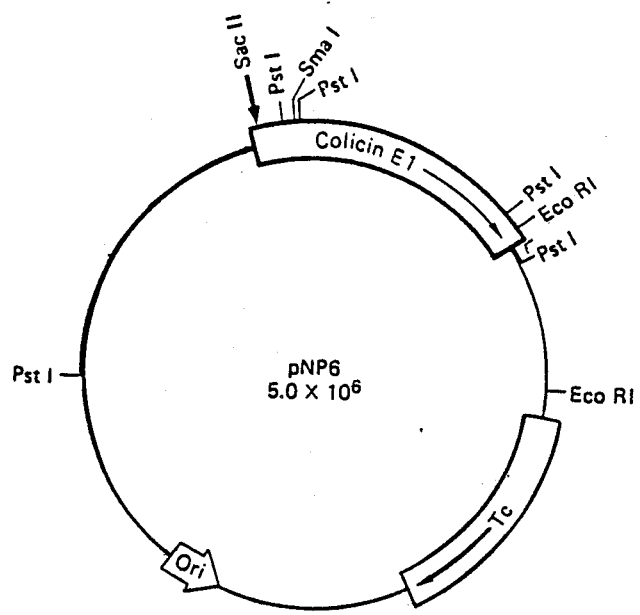
FIG. 8 is a diagram of the plasmid cloning vector pNP6 that is used in making an expression vector containing the synthetic gene of FIG. 5.

Restriction analysis using PstI was used to establish the size of the fragment(s) insert in the PstI site of the pBR322 portion of the recombinant plasmids. FIG. 8 is a restriction map of the recombinant plasmid, designated pNP6, of one of the transformed clones. A sample of this transformed clone, designated NP6-294, was deposited in the ATCC on 24 August 1983. This sample was assigned ATCC accession no. 39418. This deposit is under the Budapest Treaty and will be maintained and made accessible to others in accordance with the provisions thereof.

E. coli strain NP6-294 (pNP6) was grown and plasmid DNA isolated as described above for ColE1. The supercoiled DNA was further purified by adjusting 500 μg of DNA to 3.9 ml of TEN buffer and adding 3.45 g CsCl and 0.1 ml ethidium bromide stock solution (5 mg/ml). The mixture was transferred into a cellulose nitrate tube for an SW50.1 rotor (Beckman) and centrifuged at 36,000 rpm at 10° C. for 40 hr. The plasmid DNA band was located under a longwave UV light and was removed with a syringe by puncturing the tube from the side. The DNA sample was extracted five times with butanol and dialyzed against 100 volumes (×3) of TEN buffer for 24 hr at 4° C. The DNA was then precipitated with 2.5 volumes of ethanol and 1/10 volume of 3M sodium acetate.

PREPARATION OF DERIVATIVE PNP6ΔRI

Plasmid pNP6 contains two EcoRI restriction sites, one located in the carboxy terminal region of the colicin El gene, the other located near the tetracycline resistance gene of the original pBR322 vector. A derivative of pNP6 lacking the second site was constructed as follows. pNP6 was digested with EcoRI under limited reaction conditions so that linear molecules (cleaved at only one of the two sites) were produced. Linear molecules of pNP6 were purified by agarose gel electrophoresis and subsequently reacted with DNA polymerase I and deoxyribonucleotide triphosphates to fill in the single-stranded ends. The resulting molecules were circularized in a blunt-end ligation reaction using T4 ligase and were used to transform E. coli 294 as described previously.

Colicin-producing transformants were selected as described previously. DNA was isolated from individual clones and digested with EcoRI to identify those that contained a single, intact EcoRI site within the colicin gene. The location of the single EcoRI site was confirmed by additional restriction endonuclease mapping.

PREPARATION OF DERIVATIVE PNP6-LBR

Figure 9:
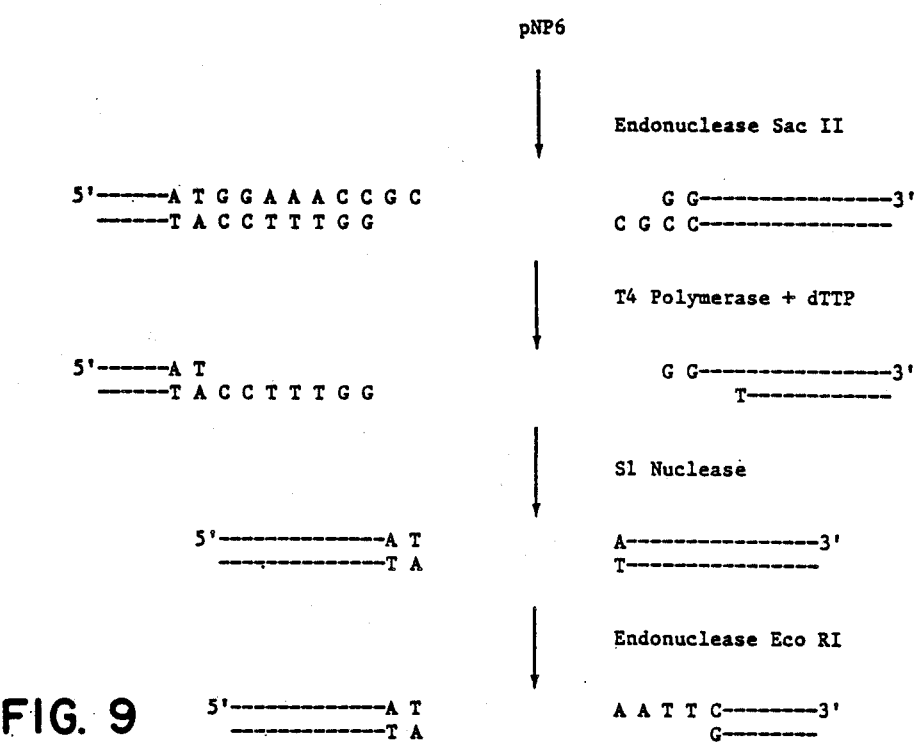
FIG. 9 is a schematic flow diagram for preparing a linearized derivative of pNP6, pNP6-LBR, that is ligated with a DNA fragment containing the synthetic CTAP-III gene or genes encoding CTAP-III analogs.

FIG. 9 outlines the steps used to prepare pNP6-LBR from pNP6. pNP6 was digested with SacII by mixing 40 μl of DNA (90.61 μg/μl), 10 μl distilled water, 50 μl of 2×SacII buffer (15 mM Tris-HCl, pH 7.5, 10 mM MgCl$_2$, 10 mM β-mercaptoethanol, 200 μg/ml BSA, and 3 μl SacII (10 U/μl)). The reaction mixture was incubated at 37° C. for 8 hr and extracted with phenol/chloroform (3:1).

The DNA was then precipitated with ethanol and redissolved in 100 μl of a solution containing 50 mM Tris-HCl (pH 8.5), 7 mM MgCl$_2$, 10 mM -βmercaptoethanol, 15 mM ammonium sulfate, 7 mM Na$_2$EDTA, 20 μg BSA, and 0.1 mM dTTP. One unit of T4 DNA polymerase (BRL) was added, and the reaction mixture incubated at room temperature for 10 min. The reaction was stopped by addition of 25 μl of 0.2 m Na$_2$ EDTA. The solution was purified of dTTP by binding the DNA in 0.12M sodium phosphate (PB), 15% formamide, to 0.5 g of hydroxyapatite at 65° C., washing with 30 ml of 0.12M PB, eluting the DNA with 0.5M PB, dialyzing against water, and precipitating with ethanol.

DNA was dissolved in a 50 μl solution containing 30 mM sodium acetate (pH 4.6), 50 mM NaCl, 1 mM ZnSO$_4$ and 5% glycerol. Two units of S1 nuclease was added and the mixture incubated at room temperature for 5 min. EDTA was added to give a final concentration of 10 mM, and the solution was extracted with phenol/chloroform (3:1) and precipitated with ethanol. The DNA was redissolved in a 50 μl solution containing 100 mM Tris-HCl (pH 7.4), 5 mM MgCl$_2$, 2 mM β-mercaptoethanol, and 50 mM NaCl. Five units of EcoRI was added and the mixture was incubated at 37° C. for 6 hr. The reaction was stopped by adding 15 μl of 0.1M EDTA and 5 μl of 10% SDS. The large plasmid fragment, pNP6-LBR, was purified by electrophoresis on a 1% agarose gel for 4 hr at 5 V/cm. The DNA fragments were visualized under longwave UV light after staining the gel for 15 min with 1 μg/ml ethidium bromide. The DNA-band (pNP6-LBR) was cut out of the slab gel, and the DNA electroeluted into a dialysis bag. The DNA was further purified by binding to a 1-cm column of diethylaminoethyl (DEAE) cellulose, washing with 0.15M NaCl, eluting with 1M NaCl, and precipitating with ethanol. The DNA was finally dissolved in TEN beffer and stored at −85° C. until used.

PREPARATION OF CTAP-III-LEU21 GENE INSERT FOR LIGATION WITH PNP6-LBR

Figure 10:
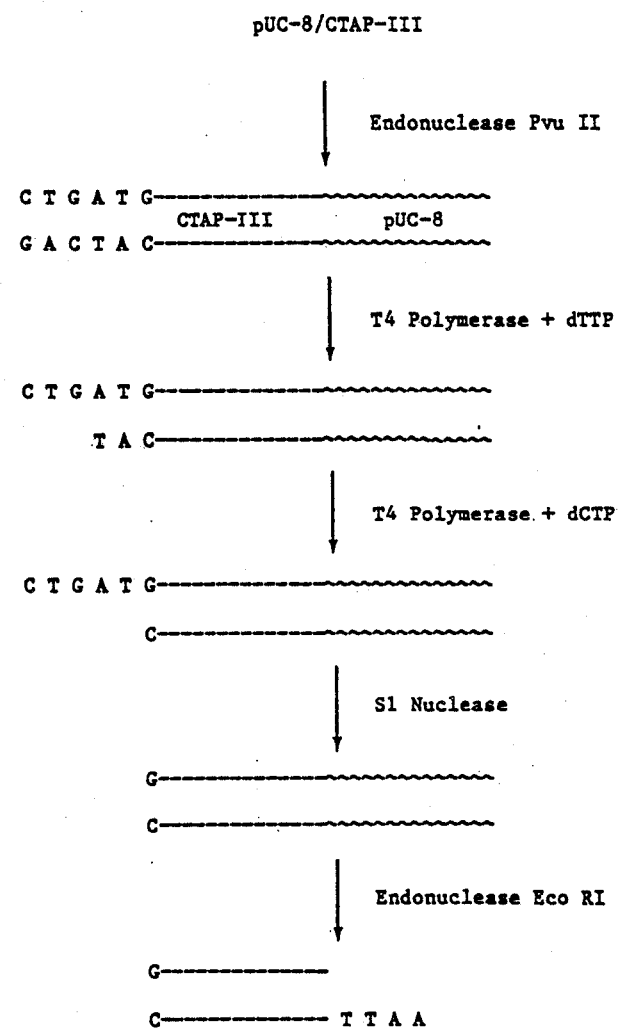
FIG. 10 is a schematic flow diagram for making the CTAP-III-Leu21 gene insert for ligation with pNP6-LBR to make the inducible plasmid expression vector of the invention.

FIG. 10 outlines the steps involved in preparing the insert DNA from pUC8/CTAP-III-Leu 21.

Plasmid pUC8/CTAP-III-Leu21 DNA was purified by the same procedure as was used to purify pNP6. Following precipitation with ethanol, 10 μg of the DNA was dissolved in a solution containing 10 mM Tris-HCl (pH 7.5), 6 mM MgCl$_2$, 6 mM β-mercaptoethanol, 50 mM NaCl, and 100 μg/ml BSA. Five units of PvuII were added and the mixture was incubated at 37° C. for 3 hr. The DNA was extracted with phenol/chloroform (3:1) and precipitated with ethanol.

Enzyme reactions using T$_4$ polymerase (with dTTP and dCTP individually), S1 nuclease, and endonuclease EcoRI were performed as described above for pNP6 vector DNA. The resulting fragment has one blunt end and one cohesive EcoRI end. Ligation of the blunt end of this fragment to the blunt end of pNP6-LBR forms a start condon, ATG, in phase with the structural gene for CTAP-III-Leu21.

PREPARATION OF EXPRESSION PLASMID PNP6-LBR/CTAP-III-LEU21

Approximately 1 pmol each of vector pNP6-LBR and the CTAP-III-Leu21 gene insert were ligated in a 100 μl reaction, transformed into E. coli 294, and selected with tetracycline, using the general procedures described above under "Cloning of the Synthetic CTAP-III Fragment in pUC8". Colonies that contain recombinant plasmid were screened by detecting the loss of ability to produce colicin El.

Single colonies were spotted on L-agar plates and incubated at 37° C. overnight. The colonies were killed by exposing them to chloroform vapor, and then were overlayed with 5 ml L-broth containing 0.7% agar and 0.1 ml of an overnight culture of E. coli K-12, CL142. After the agar hardened, the plates were incubated at 37° C. overnight. Colonies with a zone of inhibition around them were scored as colicin producers. Colonies that produced no zone contain the recombinant plasmid as demonstrated by analyzing a cleared lysate by agarose gel electrophoresis, as described above. Recombinant DNA was isolated and digested individually with restriction endonucleases BamHI, XbaI, and PstI. The fragment patterns confirmed the identify of the CTAP-III-Leu21 gene insert. One of the transformants containing the CTAP-III-Leu21 gene insert was designated pNP6-LBR/CTAP-III-Leu21.

PREPARATION OF EXPRESSION PLASMID PUC8-COL/CTAP-III-LEU21

Purified plasmid pNP6-LBR/CTAP-III-Leu21 was digested with endonuclease PstI to produce two fragments, the smaller of which (~2100 bp) contains the colicin regularity region and the CTAP-III-Leu21 structural gene. This fragment was purified and cloned into the single PstI site of plasmid pUC8 and transformants were selected with ampicillin. The resulting recombinant plasmid designated pUC8-Col/CTAP-III-Leu21 has a greater than tenfold increase in copy number than pBR322 and thus provides substantially greater quantities of CTAP-III-Leu21 upon induction, due to a gene dosage effect.

INDUCED SYNTHESIS OF CTAP-III OR CTAP-III ANALOGS

Strains pNP6-LBR/CTAP-III-Leu21 or UC8-Col/-CTAP-III-Leu21 were grown in 10 ml of L-broth medium overnight at 37° C. without aeration. The cultures were then diluted 1:100 into fresh L-broth medium and incubated at 37° C., with aeration, until the cell density reached approximately $5 \times 10^8$ cells/ml ($OD_{600}=0.6$). At this time, mitomycin C was added to a final concentration of 2 µg/ml and the incubation was continued for an additional 3.5 hr. The culture was cooled to 0° C., and cells were collected by centrifugation at 6,000 rpm for 15 min using the GSA rotor and a Sorvall centrifuge. The cell pellet was stored frozen at −85° C.

These growth conditions provide greater than 10 mg of CTAP-III-Leu21 per liter of culture in the case of UC8-Col/CTAP-III-Leu21.

After inducing the cells to produce CTAP-III/C-TAP-III analog, the CTAP-III/CTAP-III analog is worked up from the cells. The cells are first optionally killed by heating or adding an easily removed cytotoxic agent to the culture medium and then concentrated, if necessary, by filtration or centrifugation. The cell wall is then disrupted by conventional procedures such as sonication, homogenization, lysis, or pressure cycling. Particulate matter may be removed from the disruptate by filtration or centrifugation. Nucleic acids are removed from the liquid phase of the disruptate by conventional procedures such as precipitation or chromatography. The CTAP-III or analog is then recovered by the same techniques that are used to purify it from human platelets.

PREPARATION OF EXPRESSION PLASMID PNP6/CTAP-III-NMOD

Figure 11A:
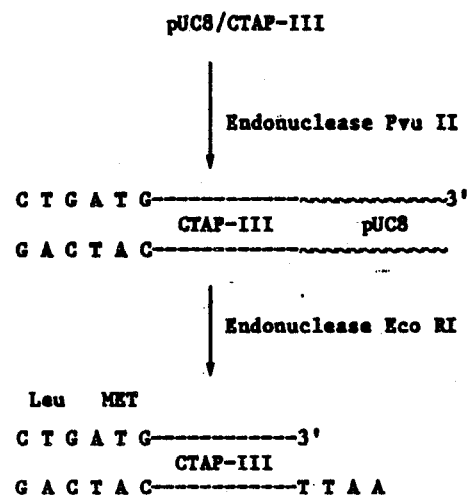
FIG. 11 is a schematic flow diagram of the procedure used to make the expression plasmid pNP6/CTAP-III-NMOD.
Figure 11B:
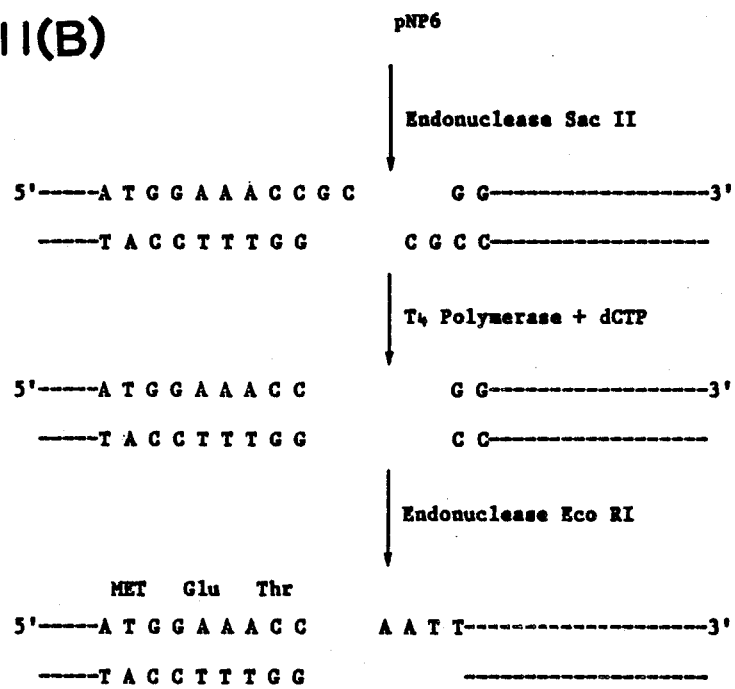
Figure 11C:
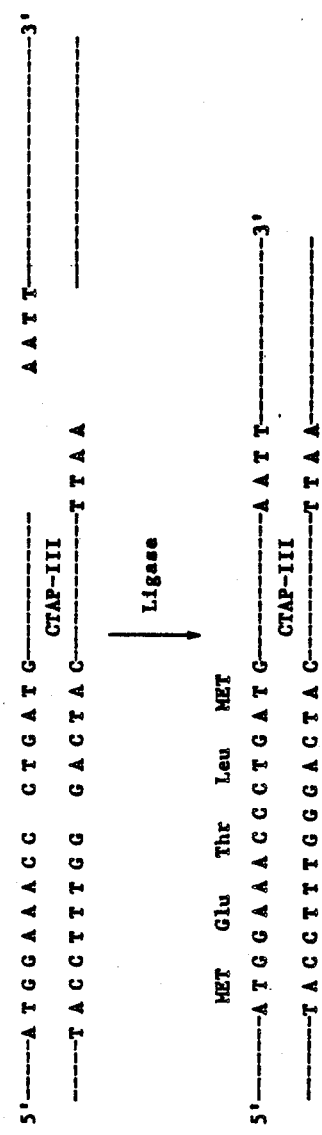

FIG. 11 outlines the steps involved in preparing pNP6/CTAP-III-NMOD from pUC8/CTAP-III-Leu21 and pNP6.

Purified pUC8/CTAP-III-Leu21 plasmid DNA was digested to completion with endonuclease PvuII, followed by endonuclease EcoRI. The products were separated by agarose gel electrophoresis, and the 273 bp fragment containing the CTAP gene was electroeluted, extracted with phenol, and precipitated with ethanol (part (A) of FIG. 11). Purified pNP6 plasmid DNA was digested to completion with endonuclease SacII, followed by treatment with $T_4$ polymerase and deoxycytidine triphosphate to remove the 3' single-stranded ends. The product of this reaction was digested with endonuclease EcoRi and the large DNA fragment produced was purified by agarose gel electrophoresis (part (B) of FIG. 11).

The final products of parts (A) and (B) were mixed in an equimolar ratio and ligated with $T_4$ ligase (part (C) of FIG. 11). The reaction mixture was used to transform E. coli 294, and several tetracycline-resistant transformants were selected. Plasmid DNA from these clones was analyzed by restriction endonuclease digestion and DNA sequence analysis to identify recombinants having the correct structure.

PREPARATION OF EXPRESSION PLASMID PNP6ΔRI/COL:CTAP III-LEU21

Figure 12A:
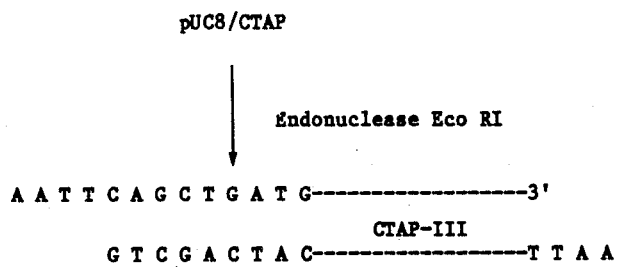
FIG. 12 is a schematic flow diagram of the procedure used to make the expression plasmid pNP6ΔRI/Col:-CTAP-III-Leu21.
Figure 12B:
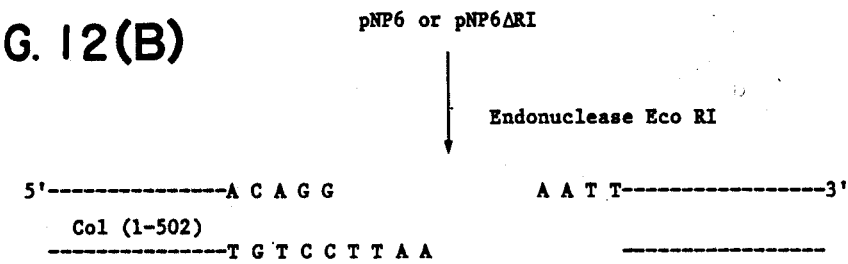
Figure 12C:
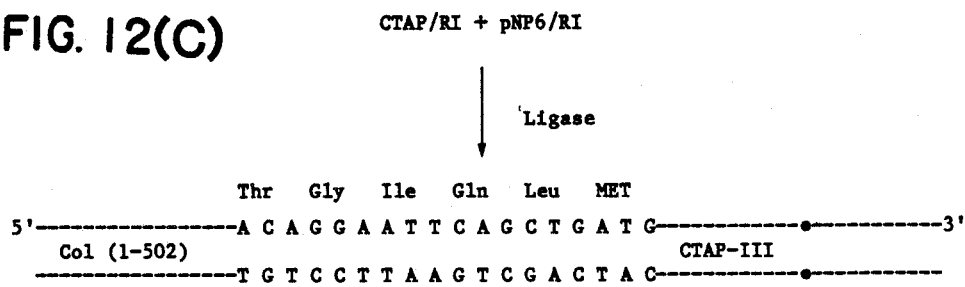

FIG. 12 outlines the steps involved in preparing pNP6ΔRI/CTAP-III-Leu21 from pUC8/CTAP-III-Leu21 and pNP6ΔRI.

Purified pUC8/CTAP-III-Leu21 plasmid DNA was digested to completion with endonuclease EcoRI to produce the 284 bp fragment containing the CTAP-III gene. This fragment was purified by agarose gel electrophoresis (part (A) of FIG. 12). Purified plasmid pNP6ΔRI (or pNP6) was digested to completion with endonuclease EcoRI and the vector fragment was purified by agarose gel electrophoresis (part (B) or FIG. 12).

The final products of parts (A) and (B) were mixed in equimolar amounts, ligated, and transformed into E. coli 294. DNAs from tetracycline-resistant transformants were analyzed by endonuclease BamHI digestion to distinguish the two possible orientations of the CTAP-III fragment within the vector DNA. The correct orientation produces a fusion product of the CTAP-III protein with amino acid residues 1–502 of colicin El (part (C) of FIG. 12).

SYNTHESIS OF CTAP-III-NMOD

Induction of CTAP-III-NMOD synthesis and its purification are accomplished as described previously for CTAP-III-Leu21, using cells containing the expression plasmid pNP6/CTAP-III-Leu21-NMOD. The amino acid sequence of CTAP-III-NMOD is depicted in FIG. 1 with the pentapeptide addition to the amino terminus shown in braces. The terminal methionine of the illustrated pentapeptide is present as a result of the bacterial production of the protein. It will be appreciated that this methionine may be absent due to post-expression processing.

SYNTHESIS OF FUSION PROTEIN OF COLICIN-CTAP-III-LEU21

Induction of Col:CTAP-III-Leu21 synthesis is accomplished as described previously for CTAP-III-Leu21, using cells containing the expression plasmid pNP6/Col:CTAP-III-Leu21.

PURIFICATION AND CLEAVAGE OF FUSION PROTEIN

Cell extracts containing CTAP-III-Leu21 fused to ColEl(1-502) (Col:CTAP-III-Leu21) were prepared by lysing cells in 50 mM sodium borate, pH 9.5, at a concentration of $1-5 \times 10^{10}$ cells/ml. Cellular debris was removed by centrifugation. Col:CTAP-III-Leu21 was purified by either of two methods using cation-exchange chromatography:

(1) 1 gram of CM-Sephadex C-50 (equilibrated with 50 mM sodium boroate, pH 9.5) was added to 100 ml of cell extract and stirred gently overnight at 4° C. The resin was collected by filtration and washed extensively with buffer until no further release of protein was detected by absorbance measurements at 280 nm. The Col:CTAP-III-Leu21 was eluted with buffer containing 0.4 M NaCl.

(2) Col:CTAP-III-Leu21 was purified from cell extracts using the Pharmacia fast protein liquid chromatography (FPLC) system. 10 to 100 ml of extract was applied to a mono S column in 50 mM sodium borate, pH 9.5, and eluted with a linear gradient of 0 to 0.5M NaCl. The fusion protein eluted at approximately 0.25M NaCl.

Purity of Col:CTAP-III-Leu21 prepared by either method was generally greater than 90%, as judged by analysis using polyacrylamide gel electrophoresis under denaturing conditions.

Purified fusion protein was dialyzed extensively against distilled water, and lyophilized. The protein was dissolved in 70% formic acid; cyanogen bromide was added at a ratio of 300 moles of cyanogen bromide per mole of methionine (approximately 2 mg cyanogen bromide per mg of fusion protein).

Samples were incubated at room temperature for 22 hr. The reaction mixture was then diluted with two volumes of distilled water and lyophilized. This cycle was repeated one to two times to remove the acid and cyanogen bromide. Finally, the protein was dissolved in 50 mM sodium phosphate, pH 6.2, and purified by FPLC using the mono S column. Protein was separated by gradient elution with phosphate buffer, pH 6.2, from 0 to 0.5M NaCl. Purified CTAP-III-Leu21 eluted between 0.2 and 0.3M NaCl.

CONVERSION OF CTAP-III-LEU21 TO β-THROMBOGLOBULIN-LEU17 (β-TG-LEU17)

CTAP-III-Leu21 can be converted to β-TG-Leu17 by proteolytic cleavage of the amino terminal tetrapeptide at Lys4-Gly5 using either plasmin or trypsin and the following protocol.

Approximately 0.5 mg/ml of CTAP-III-Leu21 in 0.15M NaCl/0.01M Tris-HCl, pH 7.5 is incubated at 37° C. for 1 hr with 1.5 I.U./ml plasmin or for 10 min with 0.5% w/w trypsin. β-TG-Leu17 is purified by FPLC using a mono S column as described above.

The purified CTAP-III or CTAP-III analogs will typically be formulated with conventional pharmaceutically acceptable carriers for administration to humans to regenerate connective tissue (e.g., heal wounds). It will usually be administered topically at the desired site of regeneration using conventional topical formulations such as creams, pastes, gels, sprays, ointments, and salves. Carriers used in such formulations are well known and include, without limitation, petrolatum, polyethylene glycol, gelatin, isopropyl myristate, polyvinyl alcohol, and the like. Alternatively, the purified CTAP-III or analog may be administered using controlled release dosage forms which typically consists of bandages or skin patches that contain the CTAP-III or analog in a manner in which it is released at a controlled rate to the skin. The control mechanism may be diffusion, osmosis, dissolution, erosion, or iontophoresis. The topical formulation of CTAP-III or an analog may contain minor amounts of additives such as emolients, stabilizers, surfactants, skin penetration altering agents, and pigments. The concentration of CTAP-III or analog in the formulation will be correlated to the prescribed dose and surface area being treated. The concentration will normally be in the range of 0.00001% to 1% by weight of the dosage form. In any event, the amount administered is sufficient to produce the desired pharmacological effect, e.g., stimulate mitogenesis, etc., so as to facilitate wound healing.

Modifications of the above described modes for carrying out the invention that are obvious of those of skill in the technical fields related to the invention are intended to be within the scope of the following claims. For instance, it is also within the scope of the invention to incorporate the colicin El regulatory and structural gene sequences into plasmids other than pBR322 that have suitable replicatory and marker functions and suitable restriction sites. It is also possible to insert the CTAP-III or analog gene into other expression plasmids that use bacterial expression control systems other than the ColEl system to control expression of the insert. For instance vectors that use the trp expression control system or lac system may be used.

We claim:

1. A synthetic structural gene that encodes human connective tissue-activating peptide-III or a mutein thereof in which the methionine at position 21 is replaced with an amino acid having an acyclic side chain and hydrophobic properties similar to methionine wherein the gene has the DNA sequence:

```
AACCTGGCTAAAGGTAAAGAAGAATCTCTGGACT
TTGGACCGATTTCCATTTCTTCTTAGAGACCTGA

CTGACTTATACGCTGAACTGCGTTGCXTGCATCA
GACTGAATATGCGACTTGACGCAACGYACGTAGT

AAACTACTTCTGGGATCCACCCGAAAAACATCCA
TTTGATGAAGACCCTAGGTGGGCTTTTTGTAGGT

GTCTCTGGAAGTTATCGGTAAAGGCACTCACTGC
CAGAGACCTTCAATAGCCATTTCCGTGAGTGACG

AACCAGGTTGAAGTTATCGCTACTCTGAAAGACG
TTGGTCCAACTTCAATAGCGATGAGACTTTCTGC

GTCGTAAAATCTGTCTAGATCCGGACGCTCCACG
CAGCATTTTAGACAGATCTAGGCCTGCGAGGTGC

TATCAAGAAGATCGTTCAGAAAAAACTGGCTGGT
ATAGTTCTTCTAGCAAGTCTTTTTTGACCGACCA

GACGAATCTGCTGAC
CTGCTTAGACGACTG.
``` where X represents ATG or a codon for said amino acid and Y represents a nonsense codon that is complementary to X.

2. A DNA fragment for use in microbially producing human connective tissue-activating peptide-III or a mutein thereof in which the methionine at position 21 is replaced with an amino acid having an acyclic side chain and hydrophobic properties similar to methionine consisting of the structural gene of claim 1 preceded by the base pair

G
C and terminated by an adaptor fragment having the sequence

TAATGACTGCAG
ATTACTGACGTCTTAA.

3. A recombinant plasmid expression vector comprising:
(a) a bacterial expression control sequence:
(b) the structural gene of claim 1 downstream under the transcriptional and translational control thereof; and
(c) a translation start codon preceding the structural gene and a translation stop codon terminating the structural gene.

4. E. coli transformed with the plasmid expression vector of claim 3 and progeny thereof.

5. A process for making connective tissue-activating peptide-III or a mutein thereof in which the methionine at position 21 is replaced with an amino acid having an acyclic side chain and hydrophobic properties similar to methionine comprising growing the E. coli of claim 4 in a culture medium and inducing the expression of the peptide or mutein thereby by adding an SOS system activating agent to the culture medium.

6. The synthetic structural gene of claim 1 wherein the gene encodes said mutein and X represents a codon for leucine, isoleucine or valine.

7. A recombinant plasmid expression vector comprising:
(a) a bacterial expression control sequence;
(b) the structural gene of claim 6 downstream of and in phase with the expression control sequence and under the transcriptional and translational control thereof; and
(c) a translation start codon preceding the structural gene and a translation stop codon terminating the structural gene.

8. The synthetic structural gene of claim 1 wherein the gene encodes said mutein and X represents the codon CTG.

9. A recombinant plasmid expression vector comprising:
(a) a bacterial expression control sequence;
(b) the structural gene of claim 8 downstream of and in phase with the expression control sequence and under the transcriptional and translational control thereof; and
(d) a translation start codon preceding the structural gene and a translation stop codon terminating the structural gene.

10. E. coli transformed with the plasmid expression vector of claim 9 and progeny thereof.

11. The synthetic structural gene of claim 1 wherein the gene is preceded by sense codons that encode the pentapeptide met glu thr leu met.

12. The synthetic structural gene of claim 1 wherein the following sequence is ligated to the 5'end of the gene:

ATGGAAACCCTGATG
TACCTTTGGGACTAC

* * * * *